United States Patent
Studin

(10) Patent No.: US 8,309,081 B2
(45) Date of Patent: Nov. 13, 2012

(54) COMPOSITION AND METHOD FOR TREATMENT OF BRUISING

(75) Inventor: Joel R. Studin, Great Neck, NY (US)

(73) Assignee: Scarguard Labs, LLC., Great Neck, NY (US)

( * ) Notice: Subject to any disclaimer, the term of this patent is extended or adjusted under 35 U.S.C. 154(b) by 561 days.

(21) Appl. No.: 12/273,311

(22) Filed: Nov. 18, 2008

(65) Prior Publication Data

US 2010/0124549 A1    May 20, 2010

(51) Int. Cl.
*A61K 38/46* (2006.01)
*C12N 9/00* (2006.01)

(52) U.S. Cl. ..................... 424/94.65; 435/183

(58) Field of Classification Search .................. 435/183; 424/94.65

See application file for complete search history.

(56) References Cited

U.S. PATENT DOCUMENTS

| | | | |
|---|---|---|---|
| 5,260,287 A | 11/1993 | Barreto et al. | |
| 5,441,740 A * | 8/1995 | Ozlen | 424/401 |
| 6,579,543 B1 | 6/2003 | McClung | |
| 7,205,007 B2 | 4/2007 | Lane | |
| 2004/0131579 A1 | 7/2004 | Duraiswami et al. | |
| 2006/0110415 A1 | 5/2006 | Gupta | |
| 2007/0160591 A1 | 7/2007 | Lane | |
| 2007/0243132 A1 | 10/2007 | Russell-Jones et al. | |
| 2008/0213246 A1 | 9/2008 | Ziff et al. | |

OTHER PUBLICATIONS

Sabahelkhier et al. 2008; www.mattclifton.com/semi-micro/.*
Pineapple Nutrition Fact 2011; www.philippineherbalmedicine.org/pineapple.htm.*
Steadman et al. 2001; Minerals, phytic acid, tannin, and rutin in buckwheat seed milling fractions. Journal of Science and Food Agriculture. 81:1094-1100.*
Jones et al. 2005; Comparison of endoproteinases in various graines. Cereal Chemistry 82(2):125-130.*
Leopoldini et al. 2006; Iron Chelation by the powerful antioxidant flavonoid Quercetin. J. Agric. Food Chem. 54: 6343-6351.*

* cited by examiner

*Primary Examiner* — Karen Cochrane Carlson
(74) *Attorney, Agent, or Firm* — Stuart D. Frenkel; Frenkel & Associates, PC.

(57) ABSTRACT

There is provided a skin treatment composition for oral or topical administration and a method for skin treatment. The composition comprises a chelating agent and at least one protease. The composition helps to remove hemosiderin that causes staining of skin on a bruised area and reduces inflammation and pain.

16 Claims, No Drawings

COMPOSITION AND METHOD FOR TREATMENT OF BRUISING

This invention relates generally to skin treatment compositions and methods of skin treatment. Specifically, this invention relates to compositions and methods for skin treatment, wherein the compositions may be administered orally or topically. More specifically, this invention relates to compositions and methods for treatment of bruising, swelling and pain that often occurs after surgery or skin injury.

DESCRIPTION OF THE RELATED ART

It is common that after surgery or skin injury bruising (ecchymosis) occurs that can be very unappealing and long lasting. Surgical procedures that can cause bruising include facelifts, rhinoplasty, liposuction, breast surgery and maxillofacial and orthopedic surgeries among others. Procedures involving injection of a filler or Botox can also cause bruising. Bruising, especially on face, has a traumatic impact on a person, particularly if it was a result of skin injury. Usually there is pain and swelling associated with bruising that causes significant discomfort to a patient or a victim of an accident.

Specifically, the appearance of bruises is caused to a large extend by hemosiderin left over from blood. Hemosiderin is an abnormal microscopic pigment composed of iron oxide that can accumulate in different organs in various diseases or conditions. During skin injury or surgery the skin experiences a shock that breaks small blood vessels. When blood leaves a ruptured blood vessel, the red blood cells die and the hemoglobin is released from them into the extracellular space. White blood cells called macrophages engulf the hemoglobin to degrade it, producing hemosiderin and porphyrin. Hemosiderin accumulated under the skin causes black, blue and reddish appearance of a bruise.

Patients and injury victims are concerned about the length of the recovery time after the injury or surgery, the appearance of bruises and the lengthy time necessary for the bruises to become less visible and eventually to be cleared completely.

Topical formulations directed towards improvement of bruising have been known. For example U.S. Publication 2007/0243132 A1 to Russell-Jones et al. discloses microemulsions to be delivered transdermally with a purpose of treating inflammations associated with bruising. U.S. Publication 2004/0131579 A1 to Duraiswami et al. discloses a topical composition that is meant to reduce the duration and severity of bruising. Nutritional supplements meant to improve healing after surgery or injury have also been known (e.g. U.S. Pat. No. 7,205,007 B2 and U.S. Publication 2007/0160591 A1 to Lane). These formulations do not address the basic problem that causes the staining of the skin. They do not help to remove hemosiderin left over from blood from ruptured blood vessels There is a need for an anti-inflammatory and pain reducing composition and method directed towards removal of hemosiderin that causes the coloring of a bruise so that it is removed easily from the bruised area and the duration of bruising is shortened. Such a composition should comprise preferably natural ingredients so that conventional medicines could be used safely at the same time during treatment. It should be formulated for either oral or topical delivery. Compositions that are to be administered orally would be particularly beneficial for the intended purpose as formulations applied to skin can be subjected to easy removal or oxidation of active ingredients before they are absorbed by skin.

SUMMARY OF THE INVENTION

The object of the invention is to provide a homeopathic skin treatment composition and method that minimize bruising and help to shorten the duration of bruising.

There is provided a skin treatment composition for oral or topical administration comprising a chelating agent and at least one protease. There is also provided a composition for oral or topical administration comprising a chelating agent, at least one protease and *Arnica montana* extract.

Additionally there is provided a method for skin treatment comprising oral or topical administration of a composition comprising a chelating agent and at least one protease. There is also provided a method for skin treatment comprising oral or topical administration of a composition comprising a chelating agent, at least one protease and *Arnica montana* extract.

DETAILED DESCRIPTION OF THE INVENTION

This invention provides a skin treatment homeopathic composition for oral or topical administration as well as a method for skin treatment, comprising oral or topical administration of the composition. The skin treatment composition of this invention reduces time that is necessary for hemosiderin to be removed from the bruise and causes the bruise coloring to fade. It also reduces inflammation and pain resulting from surgery or skin injury.

The skin treatment composition of this invention comprises a chelating agent and at least one protease. In one embodiment of the invention the chelating agent is phytic acid and the protease is bromelain. The composition may further comprise vitamins, enzymes, minerals and natural extracts.

The composition may be provided in a form of a kit. Phytic acid, a protease and the remaining ingredients may be provided in a separate dosage form and *Arnica montana* extract in a separate dosage form.

In one of the embodiments of the invention the composition includes: about 25-75 mg phytic acid, about 150-300 mg bromelain, about 50-100 mg rutin, about 2-3 mg zinc, about 30-40 mg pine bark extract, about 10-15 mcg vitamin K, about 100-150 mg vitamin C, about 30-40 I.U. vitamin E, and about 5-15 mg Coenzyme Q10. The composition may also include about 30 c *Arnica montana* extract or 1M *Arnica Montana* extract. In another embodiment the composition of this invention includes: about 50 mg phytic acid, about 250 mg bromelain, about 84 mg rutin, about 2.5 mg zinc, about 34 mg pine tree bark extract, about 12 mcg vitamin K, about 125 mg vitamin C, about 34 I.U. vitamin E, and about 8.5 mg coenzyme Q10. The composition may also include about 30 c *Arnica montana* extract or 1 M *Arnica Montana* extract.

A chelating agent that is preferably used in this invention is phytic acid. Phytic acid is a phosphorylated alcohol also known as inositol hexaphosphate or IP6 (inositol-1,2,3,4,5,6,-hexakisphosphate). It is found in whole grains, soybeans, seeds and nuts. The preferred phytic acid is the one that is 70% unbound, such as the one processed from rice bran and produced by Tsuno Foods & Rice Co., Wakayama, Japan. The highly unbound phytic acid selectively attaches to minerals as it enters the human circulatory system. It attaches to unbound compounds of iron, copper, calcium and heavy metals such as mercury, lead and cadmium. Phytic acid has little or no affinity to sodium, potassium and magnesium, the important electrolyte minerals required for maintaining the proper heart rhythm. As it enters the circulatory system it attaches to hemosiderin that remains under the skin from ruptured blood vessels and causes the staining of bruised area. Once bound to phytic acid hemosiderin is removed from the human body through the urinary track, thereby causing the staining of the skin to fade.

The protease that is preferably included in the skin treatment composition of this invention is bromelain. Bromelain, also known as bromelin, is a proteolytic anti-inflammatory enzyme naturally found in the flesh and stems of the pineapple plant, *Ananas comosus*. It is particularly effective in relieving inflammation associated with surgery and physical injuries. It helps to reduce post-operative and post-injury swelling, pain and healing time. Bromelain inhibits prostaglandins that cause inflammation, which results in swelling and pain. By slowing down those prostaglandins bromelain promotes the formation of anti-inflammatory prostaglandins that induce lessening of swelling and pain. The preferred potency of Bromelain for the purpose of this invention is 2000 GDU.

Another proteolytic enzyme that can be used in the composition of the present invention is serrapeptase, also known as serratio-peptidase or serrapeptidase. It is an enzyme extracted from *Serratia marcescens*, a bacteria found in the intestine of the silkworm. Serrapeptase is also present in fermentation extracts of *Aspergillus oryzae* and *Aspergillus melleus*, edible fungi. It is particularly useful as an anti-inflammatory as well as anti-edemic agent. It induces fibrinolytic activity in tissues thereby helping to remove blood clots. It promotes the removal of dead tissue. It generally helps with the healing process of injured tissues and reduces pain due to its ability to block the release of pain-inducing amines from inflamed tissues.

The composition of this invention is not limited to the use of phytic acid as a chelating agent. Other suitable chelating agents may be employed in the composition. Similarly other suitable proteases may be used in the composition of this invention.

Rutin, also known as rutoside, quercetin-3-rutinoside or sophorin, is a member of bioflavonoids. It is most abundant in apricots, buckwheat, cherries, prunes, rosehips, the whitish rind of citrus fruits, core of green peppers and fruit of Fava D'Anta tree. It has the ability to strengthen and modulate the permeability of the walls of the blood vessels including capillaries. It strengthens the capillaries and is especially helpful in preventing recurrent bleeding and thereby further bruising caused by weakened blood vessels such as those that were subjected to a shock during surgery or injury. It is helpful for people who bruise or bleed easily.

Zinc has anti-oxidant properties and protects the skin against premature aging. It is essential for the synthesis of collagen. It helps in production of enzymes that are necessary for repair of skin wounds and bruises. It is helpful in healing of bruises by bolstering the immune system and helping to protect the body from infections.

Pine tree bark extract is obtained from the bark of a European coastal pine tree, *Pinus maritina*. The pine tree bark is known for its antioxidant properties and for the ability to help in wound healing. It contains high amounts of bioflavonoids that have beneficial effects in improving circulation and repairing tissue. Proanthocyanidins (OPCs) that are abundant in pine tree bark extract are some of the most powerful antioxidants available. They have been shown to help reduce swelling and inflammation in the body, protect cells from radical damage and increase the effectiveness of vitamin C. Pine tree bark extract has been shown to help strengthen and repair tissues made of collagen.

Vitamin K is found naturally in leafy greens, cauliflower and liver. At least two naturally occurring forms of vitamin K have been identified and they are designated as vitamins $K_1$ and $K_2$. Both are quinone derivatives. Vitamin K is a necessary participant in synthesis of several proteins that promote blood coagulation, a property that is especially important in surgery or skin injury cases as it helps to prevent further bruising.

Vitamin C, also known as ascorbic acid, is a highly effective antioxidant. It is necessary in formation of collagen and in prevention of extensive bleeding and bruising. Thus, it promotes healing of skin tissue. Additionally it protects molecules in the body, such as proteins, lipids and carbohydrates, from damage by free radicals.

Vitamin E is a group of 8 related tocopherols and tocotrienols, of which α-tocopherol has the highest bioavailability and is the form of vitamin E that is preferentially used and absorbed by the human body. Vitamin E is a powerful antioxidant protecting body cells from free radicals. It helps with tissue repair and improves healing of wounds.

Coenzyme Q10 (CoQ10) is a coenzyme in several of the key enzymatic steps critical in the production of adenosine triphosphate (ATP), a compound essential for production of energy in every cell of the human body. Coenzyme Q10 helps to produce collagen, elastin, and other important skin molecules, thus helping to accelerate the healing process of injured skin. Additionally it functions as a powerful antioxidant. It is naturally present in organ meats such as heart, liver, kidney, as well as in beef, soybean oil, sardines and peanuts.

The composition of this invention also includes *Arnica montana* extract. *Arnica montana* is a species containing helenalin, which is a sesquiterpene lactone possessing anti-inflammatory properties especially beneficial against bruising. *Arnica montana* extract stimulates activity of white blood cells, thus causing reduction of bruising and swelling. It assists the healing process by facilitating transport of blood and fluid accumulated in the injured area through a dilating action of subcutaneous blood capillaries. It accelerates the healing of damaged tissues by encouraging immune cell function and shortens the recovery time after the surgery or injury. The composition of this invention may be formulated in various dosage forms.

For oral administration of the composition, *Arnica montana* extract may be formulated in a tablet form while a chelating agent such as phytic acid and the remaining ingredients of the composition may be included in a capsule or a tablet form.

The tablets or capsules containing chelating agent such as phytic acid and at least one protease may be provided with enteric coating. Enteric coatings are placed on tablets or capsules to ensure that the tablet or a capsule does not dissolve until it reaches the small intestine. Enteric coatings usually do not dissolve in solutions with a pH lower than 5.5. Commonly used enteric coatings include: cellulose acetate, methacrylic acid copolymers, styrol maleic acid copolymers, polymethacrylic acid/acrylic acid copolymer, hydroxypropyl methylcellulose phtalate, polyvinyl acetate phtalate, hydroxyethyl ethylcellulose phtalate, hydroxypropyl methylcellulose acetate succinate, cellulose acetate, tetrahydrophtalate, acrylic resin, and shellac. Enteric coatings are first dissolved in an organic solvent such as acetone, methanol, ethanol, isopropyl alcohol and then applied to tablets or capsules by spraying or as chemical vapor, or are put in a rotating pan partially filled with coating. The solvent is then evaporated.

Tablets and capsules may be provided in a form of a kit. If provided in a form of a kit they should be administered consecutively within a period of time as short as reasonably practicable. Tablets containing *Arnica montana* extract should be administered sublingually and should be placed under the tongue and allowed to dissolve quickly while the tablets or capsules containing chelating agent such as phytic acid and the remaining ingredients of the composition may be swallowed with water. For optimum benefit the skin treatment should start as soon as therapeutically practicable and beneficial, usually immediately after surgery or injury. An example of a single dosage is one tablet of *Arnica montana* extract and two tablets or two capsules comprising the remaining ingredients of the composition, to be taken three times per day. The daily dosage should be adjusted for each individual patient. The length of time that is necessary for the optimal results of the treatment varies with each individual case, however, the composition should be administered for at least 10 days.

For topical administration, the composition may be administered with help of a carrier in a form of an ointment, cream, lotion, gel, paste, solution, etc., and may contain liposomes, micelles, and/or microspheres. Carriers useful in this invention include any such materials known in the art that are nontoxic and do not interact with other components of the composition in a deleterious manner.

Ointments, as is well known in the art, are semisolid preparations based on petrolatum or petrolatum derivatives. The specific ointment base to be used is one that will provide for optimum delivery of the composition and will provide other desirable characteristics, for example emoliency. Ointment bases may also contain vegetable oils, fats obtained from animals or polyethylene glycols.

Creams are viscous liquids or semisolid emulsions, either oil-in-water or water-in-oil. Cream bases contain an oil phase, an emulsifier, and an aqueous phase. The oil phase generally comprises petrolatum and a fatty alcohol such as cetyl or stearyl alcohol. The aqueous phase usually exceeds the oil phase in volume and may contain a humectant. The emulsifier is generally a nonionic, anionic, cationic or amphoteric surfactant.

Gels are semi-solid suspension-type systems. Single-phase gels contain organic macromolecules distributed substantially uniformly throughout the carrier liquid, which is typically aqueous, but also, preferably, contains an alcohol and, optionally, an oil. Preferred gelling agents are crosslinked acrylic acid polymers, such as the "carbomer" family of polymers. E.g. carboxypolyalkylenes. Also preferred are hydrophilic polymers such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose and methylcellulose; gums such as tragacanth and xanthan gum, sodium alginate; and gelatin. In order to prepare a uniform gel, dispersing agents such as alcohol or glycerin can be added, or the gelling agent can be dispersed by trituration, mechanical mixing, or stirring, or combination thereof.

Lotions are preparations to be applied to the skin surface without friction and are typically liquid or semiliquid preparation in which solid particles, including the active agents are present in a water or alcohol base. Lotions are usually suspensions of solids and preferably comprise a liquid oily emulsion of the oil-in-water type. It is generally necessary that the insoluble matter in a lotion be finely divided. Lotions typically contain suspending agents to produce better dispersion as well as compounds useful for localizing and holding the active agent in contact with the skin, e.g., methylcellulose, sodium carboxymethylcellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum, hydrophilic petrolatum, or the like. The pastes made from single-phase aqueous gels generally incorporate carboxymethylcellulose or the like as a base.

Formulations for topical administration may also be prepared with liposomes, micelles, and microspheres. Liposomes are microscopic vesicles having a lipid wall comprising a lipid bilayer, and can be used for topical delivery of the present composition as well. Liposomal preparations for use in this invention include cationic, anionic and neutral preparations.

Micelles are known as comprised of surfactant molecules arranged so that their polar headgroups form an outer spherical shell, while their hydrophobic hydrocarbon chains are oriented towards the center of the sphere forming a core. Micelles form in aqueous solution containing surfactant at a high enough concentration so that micelles naturally result. Surfactants useful for forming micelles include, but are not limited to, potassium laurate, sodium octane sulfonate, sodium decane sulfonate, sodium lauryl sulfate, docusate sodium, decyltrimethylammonium bromide, dodecyltrimethylammonium bromide, tetradecyltrimethylammonium bromide, dodecyl ammonium chloride, polyoxyl 12 dodecyl ether, and nonoxynol 30. Micelle formulations can be used in conjunction with the present invention either by incorporation into the reservoir of a topical delivery system, or into a formulation to be applied to the body surface.

Microspheres may also be used for topical administration of the composition of the present invention. Similarly, like liposomes and micelles, microspheres essentially encapsulate a composition to be applied on the skin. Microspheres are generally formed from synthetic or naturally occurring biocompatible polymers, but may also be comprised of charged lipids such as phospholipids.

A carrier or a base of any form of topical delivery should be biologically and chemically inert, non-toxic, non-irritating and not interacting with components of the composition. Additionally, a carrier should provide for deep penetration of the composition into the skin.

The skin treatment composition of this invention is a homeopathic composition comprising naturally derived ingredients, which can be used safely at the same time as conventional medicines, promoting accelerated time of recovery after surgery or skin injury, and guarding against staining of skin, swelling and pain.

What is claimed is:

1. A skin treatment composition for oral or topical administration comprising a chelating agent, at least one protease, and *Arnica Montana* extract.

2. The skin treatment composition of claim 1, wherein the chelating agent is phytic acid.

3. The skin treatment composition of claim 2, wherein said protease is bromelain.

4. The skin treatment composition of claim 2, further comprising at least one of rutin, zinc, pine tree extract, vitamin K, vitamin C, vitamin E or coenzyme Q10.

5. A skin treatment composition, in the form of a kit comprising phytic acid, at least one protease and *Arnica montana* extract as a separate oral dosage form.

6. The skin treatment composition of claim 5, wherein the protease is bromelaim.

7. The skin treatment composition of claim 6, further comprising at least one of rutin, zinc, pine tree extract, vitamin K, vitamin C, vitamin E or coenzyme Q10.

8. The skin treatment composition of claim 7 comprising: about 25-75 mg phytic acid, about 150-300 mg bromelain, about 50-100 mg rutin, about 2-3 mg zinc, about 30-40 mg pine tree bark extract, about 10-15 mcg vitamin K, about 100-150 mg vitamin C, about 30-40 IU vitamin E, and about 5-15 mg coenzyme Q10.

9. The skin treatment composition of claim 8, comprising about 30 c *Arnica montana* extract.

10. The skin treatment composition of claim 9, comprising about 1 M *Arnica montana* extract.

11. The skin treatment composition of claim 5, wherein said *Arnica montana* is in a sublingual dosage form.

12. The skin treatment composition of claim 11, wherein said phytic acid and protease are combined in a single swallowable dosage form.

13. A method of skin treatment comprising oral or topical administration of a composition comprising a chelating agent, at least one protease, and *Arnica Montana* extract.

14. The method of skin treatment of claim 13, wherein the chelating agent is phytic acid and the protease is bromelain.

15. The method of skin treatment of claim 14, wherein the composition further comprises at least one of rutin, zinc, pine tree extract, vitamin K, vitamin C, vitamin E or coenzyme Q10.

16. The method of skin treatment comprising oral administration of a composition comprising phytic acid, at least one protease and as a separate oral administration *Arnica montana* extract.

\* \* \* \* \*